(12) United States Patent
Huddar et al.

(10) Patent No.: US 10,867,703 B2
(45) Date of Patent: Dec. 15, 2020

(54) SYSTEM AND METHOD FOR PREDICTING HEALTH CONDITION OF A PATIENT

(71) Applicant: Conduent Business Services, LLC, Dallas, TX (US)

(72) Inventors: Vijay Huddar, Bijapur (IN); Vaibhav Rajan, Bangalore (IN); Sakyajit Bhattacharya, Bangalore (IN); Shourya Roy, Bangalore (IN)

(73) Assignee: Conduent Business Services, LLC, Florham Park, NJ (US)

( * ) Notice: Subject to any disclaimer, the term of this patent is extended or adjusted under 35 U.S.C. 154(b) by 458 days.

(21) Appl. No.: 14/632,117

(22) Filed: Feb. 26, 2015

(65) Prior Publication Data

US 2016/0300034 A1 Oct. 13, 2016

(51) Int. Cl.
*G16H 50/30* (2018.01)
*G16H 10/60* (2018.01)

(52) U.S. Cl.
CPC ............. *G16H 50/30* (2018.01); *G16H 10/60* (2018.01)

(58) Field of Classification Search
CPC .......... G06F 17/3053; G06F 17/30864; G06N 99/005; G06N 5/022; G06N 7/005
See application file for complete search history.

(56) References Cited

U.S. PATENT DOCUMENTS

| | | | |
|---|---|---|---|
| 8,504,392 B2 | 8/2013 | Saria et al. | |
| 8,731,966 B2 | 5/2014 | Breitenstein et al. | |
| 2008/0214904 A1 | 9/2008 | Mohammed et al. | |
| 2013/0054512 A1 | 2/2013 | Ephrat et al. | |
| 2013/0329973 A1* | 12/2013 | Cao | A61B 5/0033 382/128 |
| 2014/0074509 A1 | 3/2014 | Amarasingham et al. | |
| 2015/0272509 A1* | 10/2015 | Kwon | G16H 50/50 600/518 |
| 2016/0188568 A1* | 6/2016 | Srinivasan | G06F 40/30 704/9 |

OTHER PUBLICATIONS

David Gotz, Harry Stavropoulos, Jimeng Sun, and Fei Wang. ICDA: A platform for intelligent care delivery analytics. In AMIA Annual Symposium Proceedings, vol. 2012, p. 264. American Medical Informatics Association, 2012.

(Continued)

*Primary Examiner* — Reginald R Reyes
(74) *Attorney, Agent, or Firm* — Jones Robb, PLLC (57) ABSTRACT

According to embodiments illustrated herein, there is provided a system for predicting a health condition of a first patient. The system includes a document processor configured to extract one or more headings from one or more medical records of the first patient based on one or more predefined rules. The document processor is further configured to extract one or more words from one or more phrases written under each of the extracted one or more headings, wherein the one or more phrases correspond to documentation of the observation of the first patient by a medical attender. The system further includes one or more processors configured to predict the health condition of the first patient based on a count of the one or more words in historical medical records and the one or more medical records.

9 Claims, 5 Drawing Sheets

(56) References Cited

OTHER PUBLICATIONS

Joon Lee and Roger G Mark. An investigation of patterns in hemodynamic data indicative of impending hypotension in intensive care. Biomedical engineering online, 9(1):62, 2010.

Genevieve B Melton and George Hripcsak. Automated detection of adverse events using natural lan-guage processing of discharge summaries. Journal of the American Medical Informatics Association, 12(4):448{457, 2005.

Mur HJ, FitzHenry F, Matheny ME, and et al. Automated identi_cation of postoperative complications within an electronic medical record using natural language processing. JAMA, 306(8):848{855, 2011.

Susan Rea, Jyotishman Pathak, Guergana Savova, Thomas A Oniki, Les Westberg, Calvin E Beebe, Cui Tao, Craig G Parker, Peter J Haug, Stanley M Hu_, et al. Building a robust, scalable and standards-driven infrastructure for secondary use of ehr data: The SHARPn project. Journal of biomedical informatics, 45(4):763{771, 2012.

A. L. Goldberger, L. A. N. Amaral, L. Glass, J. M. Hausdor_, P. Ch. Ivanov, R. G. Mark, J. E. Mietus, G. B. Moody, C.-K. Peng, and H. E. Stanley. PhysioBank, PhysioToolkit, and PhysioNet: Components of a new research resource for complex physiologic signals. Circulation, 101(23):e215{e220, 2000 (Jun. 13).

Himani Gupta, Prateek K Gupta, Xiang Fang, Weldon J Miller, Samuel Cemaj, R Armour Forse, and Lee E Morrow. Development and validation of a risk calculator predicting postoperative respiratory failurerisk calculator predicting respiratory failure. CHEST Journal, 140(5):1207{1215, 2011.

Jo Ann Brooks-Brunn. Predictors of postoperative pulmonary complications following abdominal surgery. CHEST Journal, 111(3):564{571, 1997.

Adam Perer and Jimeng Sun. Matrixow: Temporal network visual analytics to track symptom evolution during disease progression. In AMIA annual symposium proceedings, vol. 2012, p. 716. American Medical Informatics Association, 2012.

Ahsan M Arozullah, Jennifer Daley, William G Henderson, Shukri F Khuri, National Veterans Administration Surgical Quality Improvement Program, et al. Multifactorial risk index for predicting postoperative respiratory failure in men after major noncardiac surgery. Annals of surgery, 232(2):242, 2000.

Shahram Ebadollahi, Jimeng Sun, David Gotz, Jianying Hu, Daby Sow, and Chalapathy Neti. Predicting patients trajectory of physiological data using temporal trends in similar patients: A system for near-term prognostics. In AMIA Annual Symposium Proceedings, vol. 2010, p. 192. American Medical Informatics Association, 2010.

Ching-Tzu Huang, Horng-Chyuan Lin, Shi-Chuan Chang, and Wei-Chen Lee. Pre-operative risk factors predict post-operative respiratory failure after liver transplantation. PloS one, 6(8):e22689, 2011.

John P Ebert, Ben Grimes, and Kurt MW Niemann. Respiratory failure secondary to homologous blood transfusion. Anesthesiology, 63(1):104{106, 1985.

* cited by examiner

FIG. 4B

# SYSTEM AND METHOD FOR PREDICTING HEALTH CONDITION OF A PATIENT

TECHNICAL FIELD

The presently disclosed embodiments are related, in general, to healthcare systems. More particularly, the presently disclosed embodiments are related to a system and a method for predicting the health condition of a patient.

BACKGROUND

Healthcare industry is one industry that involves maintenance of various records from birth certificate to death certificate of a person. Such records may include, but are not limited to, one or more medical records such as nursing notes and investigative reports, and other reports comprising details of physiological parameters of the person. Further, such records may be used for predicting a health condition of a patient.

Generally, the health condition of the patient may be predicted using various heterogeneous electronic sources such discharge summaries. However, the discharge summaries are usually available only at the time of discharge of the patient. Such data may not be useful in predicting the health condition of the patient, while the patient is under medical observation (for instance, when the patient is in an intensive care unit).

SUMMARY

According to embodiments illustrated herein, there is provided a system for predicting a health condition of a first patient. The system includes a document processor configured to extract one or more headings from one or more medical records of the first patient based on one or more predefined rules, wherein each of the one or more headings correspond to one or more medical specialties supported by a medical center where the first patient is observed. The document processor is further configured to extract one or more words from one or more phrases written under each of the extracted one or more headings, wherein the one or more phrases correspond to documentation of the observation of the first patient by a medical attender. The system includes one or more processors configured to predict an occurrence of the health condition of the first patient based on a count of the one or more words in historical medical records and the one or more medical records.

According to embodiments illustrated herein, there is provided a method for predicting a health condition of a first patient. The method includes extracting, by a document processor, one or more headings from one or more medical records of the first patient based on one or more predefined rules, wherein each of the one or more headings corresponds to one or more medical specialties supported by a medical center where the first patient is observed. The method further includes extracting, by the document processor, one or more words from one or more phrases written under each of the extracted one or more headings, wherein the one or more phrases correspond to documentation of the observation of the first patient by a medical attender. The method further includes measuring, by one or more sensors, one or more physiological parameters associated with the first patient. The method further includes predicting, by one or more processors, an occurrence of the health condition of the first patient based on at least the measure of the one or more physiological parameters and a count of the one or more words in historical medical records and the one or more medical records.

According to embodiments illustrated herein, there is provided a computer program product for use with a computer. The computer program product includes a non-transitory computer readable medium. The non-transitory computer readable medium stores a computer program code for predicting a health condition of a first patient. The computer program code is executable by a document processor configured to extract one or more headings from one or more medical records of the first patient based on one or more predefined rules, wherein each of the one or more headings correspond to one or more medical specialties supported by a medical center where the first patient is observed. The computer program code is further executable by the document processor configured to extract one or more words from one or more phrases written under each of the extracted one or more headings, wherein the one or more phrases correspond to documentation of the observation of the first patient by a medical attender. The computer program code is executable to measure, by one or more sensors, one or more physiological parameters associated with the first patient. The computer program code is executable to predict, by the one or more processors, an occurrence of the health condition of the first patient based on at least the measure of the one or more physiological parameters and a count of the one or more words in historical medical records and the one or more medical records.

BRIEF DESCRIPTION OF DRAWINGS

The accompanying drawings illustrate various embodiments of systems, methods, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not to limit the scope in any manner, wherein like designations denote similar elements, and in which.

DETAILED DESCRIPTION

The present disclosure is best understood with reference to the detailed figures and description set forth herein. Various embodiments are discussed below with reference to the figures. However, those skilled in the art will readily appreciate that the detailed descriptions given herein with respect to the figures are simply for explanatory purposes as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment", "an embodiment", "at least one embodiment", "one example", "an example", "for example" and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment.

Definitions:

The following terms shall have, for the purposes of this application, the respective meanings set forth below.

A "computing device" refers to a device that includes one or more processors/microcontrollers and/or any other electronic components, or a device or a system, which performs one or more operations according to one or more programming instructions/codes. Examples of a computing device may include, but are not limited to, a desktop computer, a laptop, a personal digital assistant (PDA), a mobile device, a smartphone, a tablet computer (e.g., iPad®, and Samsung Galaxy Tab®), and the like.

A "Multi-Function Device (MFD)" refers to a device that can perform multiple functions. Examples of the functions may include, but are not limited to, printing, scanning, copying, faxing, emailing, and the like. In an embodiment, the MFD includes a scanner and a printer for scanning and printing one or more documents (i.e., medical records such as a nursing note, investigative report, and other medical notes written by healthcare professionals) respectively. In an embodiment, the MFD has communication capabilities that enable the MFD to send/receive data and messages in accordance with one or more communication protocols such as, but not limited to, FTP, WebDAV, E-Mail, SMB, NFS, and TWAIN.

A "patient" is a human being who may require medical care or treatment by a medical expert such as a doctor. In another words, a patient is any recipient of health care services. In an embodiment, a first patient refers to the patient who is currently under medical observation. In an embodiment, a second patient refers to the patient who was under medical observation in the past.

A "medical record" refers to a documentation of health condition of a patient. In an embodiment, the medical record may include a measure of physiological parameters associated with the patient, which may have been documented periodically. Further, the medical record data may include notes documented over time by a healthcare professional (a doctor, a nurse, a medical attender, etc.). In an embodiment, notes may include recorded observations, administered drugs and therapies, test results, x-rays, nursing reports, investigative reports, etc. In an embodiment, the medical record may be documented on a computing device such as, but not limited to, a desktop computer, a laptop, a PDA, a mobile device, a smartphone, a tablet computer, and the like. In an embodiment, the medical record may be an electronic or handwritten document. In case of the handwritten document (such as on a paper), the medical record may be scanned to obtained the electronic form.

A "nursing note" refers to a medical record that may describe a health condition of a patient and a treatment given or planned. The nursing note may be documented by a nurse, physician, and other healthcare professionals that usually focus on documenting the health condition of the patient. The nursing note may comprise, but not limited to, prescribed treatments, response to the prescribed treatments, or diagnosis. The nursing note corresponding to the patient are recorded daily in the hospital. Hereinafter, "nursing note" and "nursing report" may be interchangeably used.

An "investigative report" refers to a medical report that may be representative of the state and progress of a patient. In an embodiment, the investigative report may comprise, but not limited to, one or more reports from radiology, microbiology, and biochemistry. In an embodiment, the investigative reports may be periodically recorded during a patient's stay in a hospital. Hereinafter, "investigative note" and "investigative report" may be interchangeably used.

A "medical specialty" refers to a branch of medical science that specializes in a treatment of a particular type of ailment or a body part. Examples of medical specialties include, but are not limited to, Cardiology, Rheumatology, Nephrology, Neurology, Endocrinology, Hematology, Dermatology, Ophthalmology, and so on.

A "heading" refers to a word or a group of words which may be indicative of a context of a paragraph/phrases/words mentioned under such heading.

A "phrase" refers to a single word or a group of words that forms a constituent and by which it functions as a single unit in the syntax of a sentence.

"One or more predefined rules" refer to one or more conditions utilized for extracting one or more headings from one or more medical records. In an embodiment, the one or more predefined rules may be used for extracting one or more words from one or more phrases documented under the one or more headings. In an embodiment, a user may define the one or more predefined rules.

A "user" refers to a medical professional such as, but not limited to, a doctor, a nurse, a medical attendant, a hospital staff, or any other healthcare professional. In an embodiment, the user may be an individual who may not as such belong to a medical profession but may operate the computing device of the disclosure.

A "first score" refers to a numerical value assigned to each of one or more words documented under one or more headings. In an embodiment, the first score may refer to the importance value of a word. In an embodiment, the first score of a word under a heading may be determined based on a count of the words documented under the same heading in the historical medical records of the one or more second patients. For example, a word "Crocin" is documented under a heading "Head Ache" in a medical record of a first patient A. The one or more second patients include patients B and C. Hence, the first score for the word "Crocin" may be determined based on a count of the word "Crocin" under the heading "Head Ache" in the historical medical records of the patients B and C.

A "first feature vector" refers to a set of parameters (each parameter represents a feature value) associated with each of one or more words. In an embodiment, the parameter associated with each word is determined based on a count of each word in one or more medical records associated with the first patient.

A "sensor" refers to a device that detects/measures events or changes in quantities and provides a corresponding output, generally as an electrical or optical signal. In medical science, the sensor may be operable to detect biological, physical, and/or chemical signals associated with first patient and may measure and record those signals. For example, pressure sensors, temperature sensors, and humidity sensors are used to monitor and regulate gas flow and gas conditions in Anesthesia Machines, Respirators and Ventilators.

"Vital signs" refer to a measure of one or more physiological parameters that may be indicative of an individual's general health condition. The vital signs may point to potential diseases or show a recovery progress from a disease. In an embodiment, the vital signs may comprise at least blood pressure, heart rate, respiratory rate, body temperature, and oxygen saturation. Hereinafter, "vital signs" and "physiological parameters" may be interchangeably used.

A "second feature vector" refers to a set of statistical parameters determined from one or more physiological parameters associated with a first patient. In an embodiment, the statistical parameters may be determined by performing one or more mathematical operations (e.g., mean, standard deviation, median, fitting a Gaussian distribution to data, determining a linear regression on the data, etc.) on the one or more physiological parameters associated with the first patient.

Figure 1:
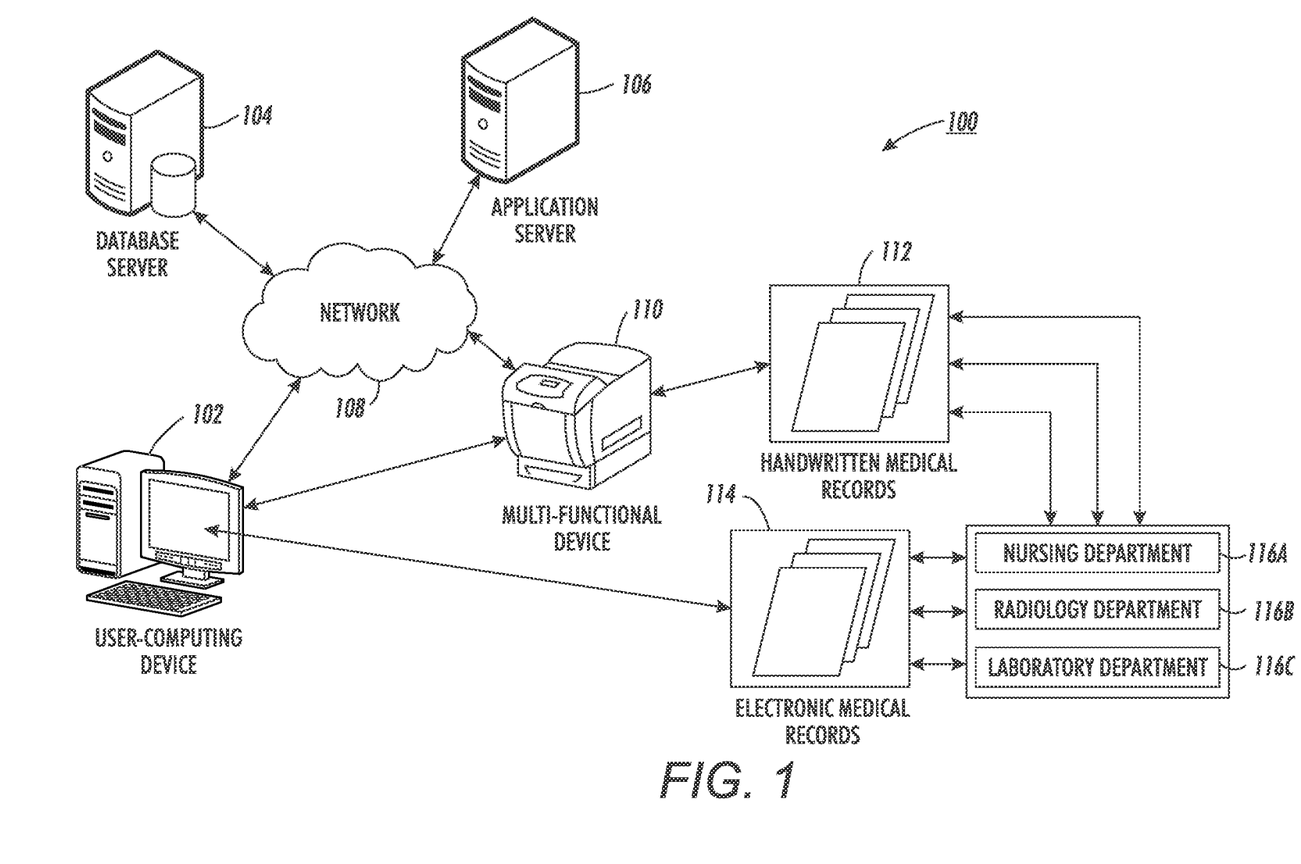
FIG. 1 is a block diagram illustrating a system environment in which various embodiments may be implemented.

FIG. 1 is a block diagram illustrating a system environment 100 in which various embodiments may be implemented. The system environment 100 includes a user-computing device 102, a database server 104, an application server 106, and a network 108. Various devices in the system environment 100 may be interconnected over the network 108. FIG. 1 shows, for simplicity, one user-computing device 102, one database server 104, and one application server 106. However, it will be apparent to a person having ordinary skill in the art that the disclosed embodiments may also be implemented using multiple user-computing devices 102, multiple database servers 104, and multiple applications servers 106.

The user-computing device 102 refers to a computing device used by a user. The user-computing device 102 may comprise one or more processors in communication with one or more memories. The user-computing device 102 may be operable to execute one or more sets of instructions stored in the one or more memories. In an embodiment, the user-computing device 102 may be communicatively coupled to the network 108. In an embodiment, the user-computing device 102 may comprise a display screen that may be configured to display one or more user interfaces to the user. In an embodiment, the user may utilize the user-computing device 102 to transmit or receive metadata pertaining to a first patient to/from the database server 104 and/or the application server 106 over the network 108. For example, the user may transmit, using the user-computing device 102, one or more medical records of the first patient. For example, the user may transmit a nursing note or an investigative note. The one or more medical records may be handwritten medical records 112 or electronic medical records 114. The one or more medical records may be received from one or more medical departments such as, but not limited to, a nursing department 116A, a radiology department 116B, and/or a laboratory department 116C. In an embodiment, the user-computing device 102 may receive the electronic medical records 114 from the one or more medical departments. In another embodiment, the user-computing device 102 may be coupled to a MFD 110. Though, the MFD 110 is implemented outside the user-computing device 102 in FIG. 1, a person skilled in the art would appreciate the MFD 110 to be depicted inside the user-computing device 102 without departing from the scope of the disclosure. Further, in an embodiment, the MFD 110 may scan the one or more medical records such as the handwritten medical records 112 to generate the corresponding electronic medical records which may be transmitted to the user-computing device 102. In an embodiment, the user may utilize the user-computing device 102 to provide one or more inputs to perform one or more operations such as, but are not limited to, scanning of a medical record (e.g., handwritten nursing note on a paper) and extracting statistical parameters from one or more vital signs. The user-computing device 102 may correspond to various types of computing devices such as, but not limited to, a desktop computer, a laptop, a personal digital assistant (PDA), a mobile device, a smartphone, a tablet computer (e.g., iPad® and Samsung Galaxy Tab®), and the like.

The database server 104 may refer to a computing device that may store historical medical records of one or more second patients, in accordance with at least one embodiment. In an embodiment, the database server 104 may store metadata pertaining to the historical medical records of the one or more second patients. The metadata pertaining to the historical medical records of the one or more second patients may comprise, but is not limited to, one or more medical complications developed during their stay in hospital, clinical notes (such as nursing notes, investigative reports, medication and allergies reports, laboratory test results, radiology images), personal statistics (such as age and weight) and other reports such as measures of vital signs. In an embodiment, the database server 104 may extract the metadata pertaining to the historical medical records from various sources such as, but are not limited to, databases of various medical organizations that may provide a rightful authentication to access the information pertaining to the one or more second patients or from publicly available databases such as MIMIC II.

In an embodiment, the database server 104 may be communicatively coupled over the network 108. In an embodiment, the database server 104 may be configured to transmit or receive one or more instructions/metadata to/from one or more devices, such as the user-computing device 102 and the application server 106 over the network 108. In an embodiment, the database server 104 may receive a query from the user-computing device 102 or the application server 106 to retrieve the metadata pertaining to the historical medical records of the one or more second patients. For querying the database server 104, one or more querying languages may be utilized such as, but not limited to, SQL, QUEL, DMX and so forth. Further, the database server 104 may be realized through various technologies such as, but not limited to, Microsoft® SQL server, Oracle, and My SQL.

The application server 106 may refer to a computing device or a software framework that may provide a generalized approach to create the application server implementation. In an embodiment, the function of the application server 106 may be dedicated to the efficient execution of procedures, such as, but not limited to, programs, routines, or scripts stored in one or more memories for supporting its applied applications. In an embodiment, the user may access the application server 106 over the network 108 to submit the one or more medical records of the first patient (e.g., through the user-interface). The one or more medical records of the first patient may include associated metadata such as, but not limited to, clinical notes (such as nursing notes, investigative reports, medication and allergies reports, laboratory test results, radiology images), personal statistics (like age and weight), and other reports such as measures of vital signs associated with the first patient. Alternatively, the application server 106 may extract the one or more medical records of the first patient from the database server 104. Further, in an embodiment, the application server 106 may transmit a query to extract the metadata pertaining to the historical medical records of the one or more second patients from the database server 104 over the network 108. In an embodiment, the application server 106 may utilize a query, a program, an algorithm, or a code to segregate the historical medical records of the one or more second patients into two classes, namely class A (e.g., the second patients who had developed medical complications during their ICU stay) and class B (e.g., the second patients who had not developed medical complications during their ICU stay). In an embodiment, the application server 106 may train one or more classifiers based on the segregated class A and class B historical medical records. The one or more classifiers may be implemented using one or more machine learning algorithms (e.g., support vector machine (SVM)). One or more processors in the application server 106 may utilize the one or more trained classifiers to predict a health condition of the first patient based on the processing of the one or more medical records of the first patient. The application server 106 may be realized using various technologies such as, but not limited to, Java application server, .NET Framework, PHP, Base4 application server, and Appaserver. The application server 106 has been described later in conjunction with FIG. 2.

A person skilled in the art would understand that the scope of the disclosure should not be limited to the database server 104 or the application server 106 as a separate entity. In an embodiment, the functionalities of the database server 104 and the application server 106 may be combined into a single server without limiting the scope of the inventions.

The network 108 corresponds to a medium through which content and messages may flow between one or more of, but not limited to, the user-computing device 102, the database server 104, and the application server 106. Examples of the network 108 may include, but are not limited to, a Wireless Fidelity (Wi-Fi) network, a Wide Area Network (WAN), a Local Area Network (LAN), or a Metropolitan Area Network (MAN). Various devices such as the user-computing device 102, the database server 104, and the application server 106, may connect to the network 108 in accordance with various wired and wireless communication protocols such as Transmission Control Protocol/Internet Protocol (TCP/IP), User Datagram Protocol (UDP), and 2G, 3G, or 4G communication protocols.

A person skilled in the art would understand that the scope of the disclosure should not be limited to the MFD 110 coupled to the user-computing device 102 as an only entity. In an embodiment, the MFD 110 may be coupled to the database server 104 or the application server 106 without limiting the scope of the disclosure. Further, in an embodiment, a person skilled in the art would appreciate the MFD 110 to be depicted inside or outside the database server 104 or the application server 106 without departing from the scope of the disclosure. Further, in an embodiment, the MFD 110 may be connected to the database server 104 or the application server 106 over the network 108 without limiting the scope of the disclosure.

Figure 2:
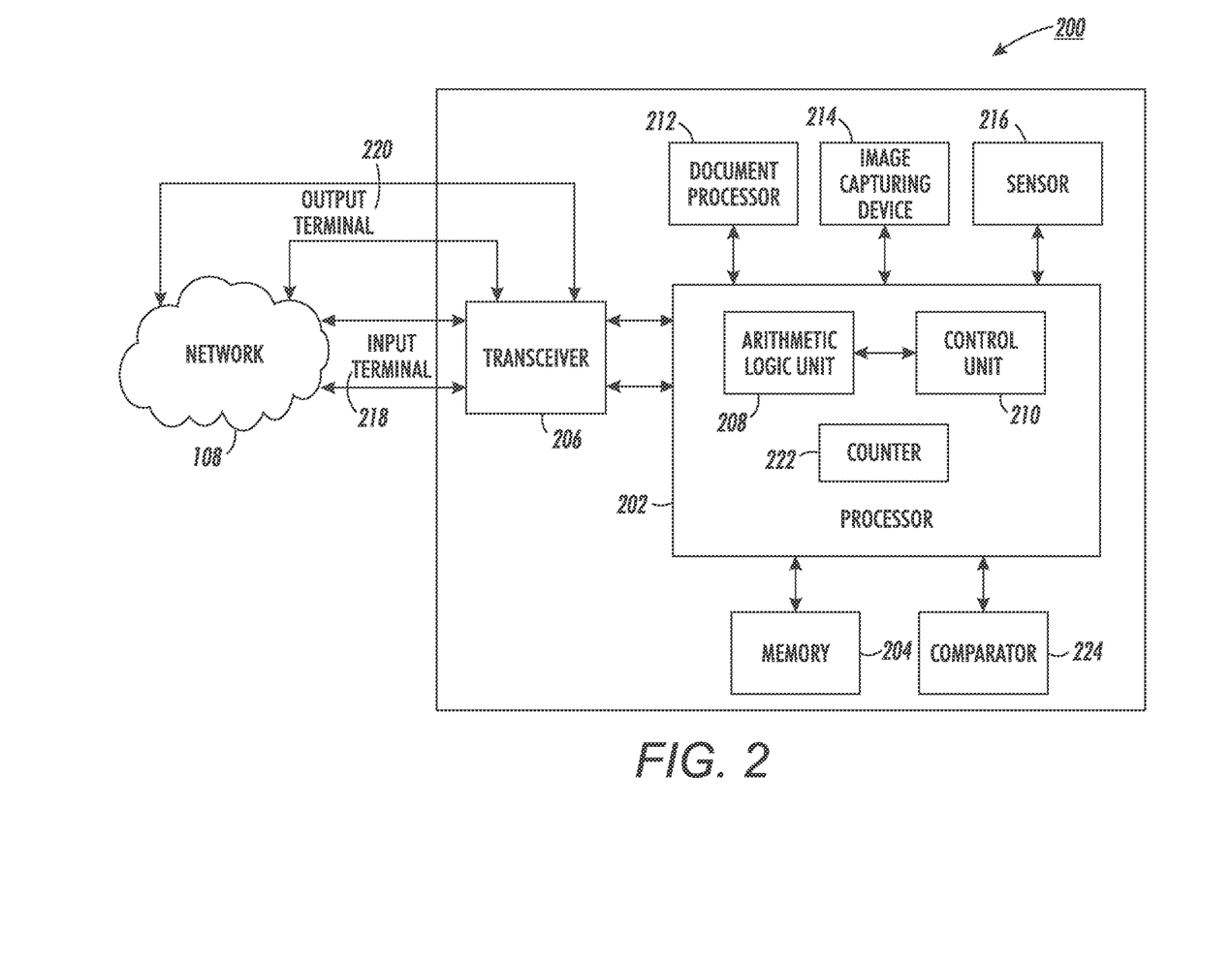
FIG. 2 is a block diagram illustrating a system for predicting health condition of a first patient, in accordance with at least one embodiment.

FIG. 2 is a block diagram illustrating a system 200 for predicting the health condition of the first patient, in accordance with at least one embodiment. The system 200 may comprise one or more processors, such as a processor 202, one or more memories, such as a memory 204, one or more transceivers, such as a transceiver 206, one or more arithmetic logic units, such as an arithmetic logic unit (ALU) 208, one or more control units, such as a control unit 210, one or more document processors, such as a document processor 212, one or more image capturing devices, such as an image capturing device 214, one or more sensors, such as a sensor 216, one or more counters, such as a counter 222, one or more comparator, such as a comparator 224. The transceiver 206 is coupled with an input terminal 218 and an output terminal 220.

The system 200 may correspond to the user-computing device 102 or the application server 106 without departing from the scope of the disclosure. For the purpose of the ongoing description, the system 200 has been considered as the application server 106.

The processor 202 may be configured to execute a set of instructions stored in the memory 204 to perform one or more operations. The processor 202 may be coupled to the memory 204, the transceiver 206, the document processor 212, the image capturing device 214, the sensor 216, and the comparator 224. The processor 202 may comprise the ALU 208 and the control unit 210. The ALU 208 may be coupled to the control unit 210. The control unit 210 controls the operation of the ALU 208. The processor 202 may comprise one or more counters such as the counter 222. The processor 202 may be implemented based on a number of processor technologies known in the art. Examples of the processor 202 include, but are not limited to, an X86-based processor, a Reduced Instruction Set Computing (RISC) processor, an Application-Specific Integrated Circuit (ASIC) processor, and/or a Complex Instruction Set Computing (CISC) processor.

The memory 204 may be operable to store one or more machine codes, and/or computer programs having at least one code section executable by the processor 202. The memory 204 may store one or more sets of instructions or metadata associated with one or more patients (first patient and/or one or more second patients). Some of the commonly known memory implementations include, but are not limited to, a random access memory (RAM), a read-only memory (ROM), a hard disk drive (HDD), and a secure digital (SD) card. In an embodiment, the memory 204 may include the one or more machine codes, and/or computer programs that are executable by the processor 202 to perform specific operations. It will be apparent to a person having ordinary skill in the art that the one or more instructions stored in the memory 204 enables the hardware of the system 200 to perform the predetermined operation.

The transceiver 206 may be operable to communicate with the one or more devices, such as the user-computing device 102, and/or one or more servers, such as the database server 104 over the network 108. The transceiver 206 may be operable to transmit or receive the metadata to/from various components of the system environment 100. In an embodiment, the transceiver 206 is coupled to the input terminal 218 and the output terminal 220 through which the transceiver 206 may receive or transmit metadata/messages/instructions associated with the one or more patients (first patient and/or one or more second patients). In an embodiment, the input terminal 218 and the output terminal 220 may be realized through, but not limited to, an antenna, an Ethernet port, an USB port or any other port that can be configured to receive and transmit data. The transceiver 206 may receive and transmit data/messages in accordance with various communication protocols such as, TCP/IP, UDP, and 2G, 3G, or 4G communication protocols through the input terminal 218 and the output terminal 220, respectively.

The document processor 212 is an electric or electronic device, or computer software application that may create structured documents. In an embodiment, the document processor 212 may be operable to analyze and process one or more documents to extract useful information. In an embodiment, the document processor 212 may be realized using one or more processors that may utilize one or more programs such as PTC Arbortext APP (formerly Advent 3B2,) Adobe FrameMaker, LyX, BroadVision QuickSilver (formerly Interleaf TPS), and Syntext Serna. In an embodiment, the document processor 212 may employ one or more image processing techniques and intelligent character recognition (ICR) techniques to process the documents.

The image capturing device 214 is a device that optically scans images, printed text, handwriting, or an object, and converts it to a digital image. In an embodiment, the image capturing device 214 may correspond to a scanner or a camera that may be utilized to scan the one or more documents (e.g., one or more nursing notes or investigative reports, etc.). In another embodiment, the image capturing device 214 may be realized using one or more MFDs such as the MFD 110. Though, the image capturing device 214 is implemented within the application server 106 in FIG. 2, a person skilled in the art would appreciate the image capturing device 214 to be depicted as independent from the application server 106 without departing from the scope of the disclosure. In an embodiment, the image capturing device 214 may further include a CMOS sensor or a CCD sensor that may be used for capturing the image of the one or more documents. In further embodiment, the image capturing device 214 may utilize raster scanning techniques to capture the image of the one or more documents.

The sensor 216 is a device that detects events or changes in quantities and provides a corresponding output, generally as an electrical or optical signal. In an embodiment, the sensor 216 may correspond to a bio-sensor, which is configured to measure the one or more physiological parameters of the first patient. In an embodiment, the sensor 216 may be inbuilt within the system 200. Alternatively, the sensor 216 may be a separate device, which may be communicatively or otherwise coupled to the system 200.

The comparator 224 is configured to compare an at least two input signals to generate an output signal. In an embodiment, the output signal may correspond to either "1" or "0". In an embodiment, the comparator 224 may generate output "1" if the value of a first signal (from the at least two signals) is greater than a value of the second signal (from the at least two signals). Similarly, the comparator 224 may generate an output "0" if the value of the first signal is less than the value of the second signal. In an embodiment, the comparator 224 may be realized through either software technologies or hardware technologies known in the art.

In operation, the processor 202 may extract the historical medical records of the one or more second patients from the database server 104. In an embodiment, the processor 202 may send a query through the output terminal 220 to the database server 104 to extract the historical medical records of the one or more second patients. In an embodiment, the transceiver 206 may receive the historical medical records of the one or more second patients through the input terminal 218. The historical medical records of the one or more second patients may be stored in the memory 204. In an embodiment, the processor 202 may segregate the historical medical records of the one or more second patients into two classes such as class A and class B historical medical records. The segregation of the historical medical records of the one or more second patients may be based on at least the medical complications developed by the one or more second patients when they were under medical observation in the hospital.

Thereafter, the processor 202 may train the one or more classifiers using the class A and class B historical medical records of the one or more second patients. In an embodiment, the processor 202 may utilize extracted one or more headings and extracted one or more words under each of the extracted headings from class A (and class B) historical medical records of the one or more second patients to train the one or more classifiers. The training of the one or more classifiers will be explained in conjunction with FIG. 3. Thereafter, the processor 202 obtains/receives the one or more medical records of the first patient who is currently under medical observation. In an embodiment, the user may utilize the image capturing device 214 or the MFD 110 to scan the one or more medical records of the first patient, when the one or more medical records of the first patient are not available in an electronic form. Thereafter, the document processor 212 may extract one or more headings from the one or more medical records of the first patient. In an embodiment, the document processor 212 may extract one or more words from one or more phrases written under each of the extracted one or more headings in the one or more medical records of the first patient.

A person having ordinary skill in the art would understand that the scope of the disclosure is not limited to obtaining the electronic form of the one or more medical records by scanning the one or more handwritten medical records such as the handwritten medical records 112. In an embodiment, the medical records may be documented in an electronic form at the first go (depicted by 114 in FIG. 1). In such a scenario, the medical attender may have a tablet device that allows the medical attender to document notes. The tablet device may have an input means (touch screen of an input pen) that facilitates the medical practitioner to write notes directly on the tablet. In an embodiment, the tablet may include a software that presents a platform to the user of the tablet to write notes. Further, the written notes may be stored in the database server 104. Further, the notes may be stored in the cloud storage. Further, the scope of the disclosure is not limited to a tablet device. In an embodiment, any computing device (such as a computer, laptop, phone, Smartphone) may be used for inputting the notes.

Post extracting the one or more words from each of the one or more headings, the ALU 208 may determine a first score associated with each of the one or more words. The determination of the first score will be explained later, in conjunction with FIG. 3. In an embodiment, the processor 202 may select a predefined number of words under each heading based on the first score. In an embodiment, the processor 202 may utilize the ALU 208 and the counter 222 to determine a first feature vector from the one or more medical records (text observation) of the first patient. In an embodiment, the processor 202 may determine a second feature vector based on one or more statistical parameters associated with each of the one or more physiological parameters associated with the patient. In an embodiment, the processor 202 may utilize one or more sensors, such as the sensor 216 to measure the one or more physiological parameters of the first patient. The determination of the first feature vector and the second feature vector will be explained later, in conjunction with FIG. 3 and FIGS. 4A and 4B.

Post determination of the first feature vector and the second feature vector, the processor 202 utilizes the one or more trained classifiers to determine/predict the health condition of the first patient.

Figure 3:
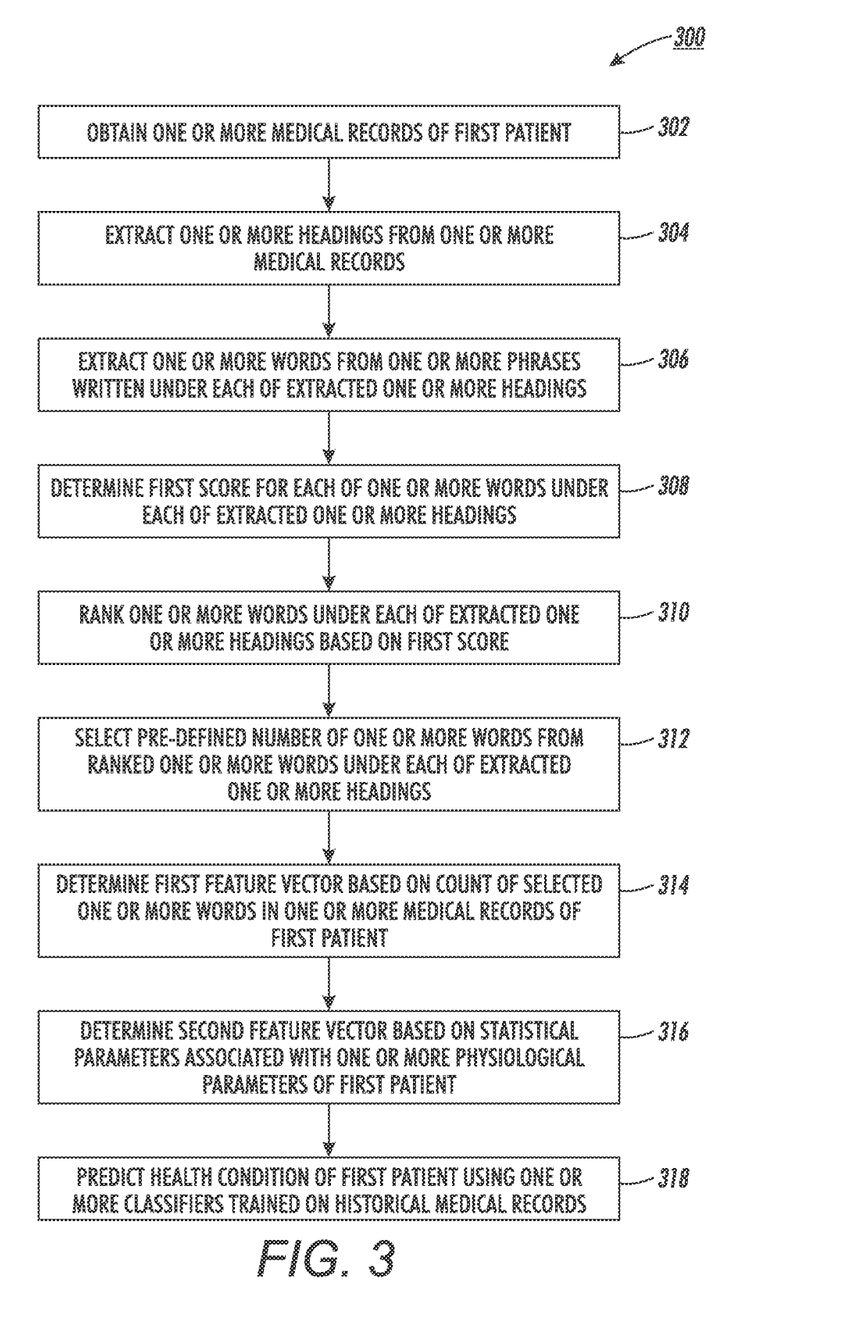
FIG. 3 is a flowchart illustrating a method for predicting health condition of a first patient, in accordance with at least one embodiment.

FIG. 3 is a flowchart 300 illustrating a method for predicting the health condition of the first patient, in accordance with at least one embodiment. The flowchart 300 is described in conjunction with FIG. 1 and FIG. 2.

At step 302, the one or more medical records of the first patient are received. In an embodiment, the processor 202 may receive the one or more medical records of the first patient, who is under medical observation, from the user-computing device 102 or the database server 104 over the network 108. The one or more medical records of the first patient may comprise, but are not limited to, one or more clinical notes, such as nursing notes, investigative reports, etc., written by one or more healthcare professionals such as, but not limited to, a doctor, a nurse, or a medical attender. In an embodiment, the one or more medical records may be documented on a computing device such as, but not limited to, a desktop computer, a laptop, a PDA, a mobile device, a smartphone, a tablet computer, and the like. However, the one or more medical records may be available either in the form of an electronic or handwritten record (such as one that is written with a pen and paper). In an embodiment, the handwritten medical records 112 may be scanned by utilizing the MFD 110 before transmitting it to the user-computing device 102. In case of the handwritten medical records (which may be stored in the database server 104), the processor 202 may utilize the image capturing device 214 to scan the one or more handwritten medical records associated with the first patient.

In an embodiment, the processor 202 may further receive the one or more physiological parameters such as, but not limited to, blood pressure, heart rate, respiratory rate, body temperature, and oxygen saturation, of the first patient. In an embodiment, the processor 202 may receive the one or more physiological parameters from the user-computing device 102 or the database server 104 over the network 108. In an embodiment, the processor 202 may utilize the sensor 216 to measure the one or more physiological parameters of the first patient.

In an embodiment, the processor 202 may further extract the historical medical records of the one or more second patients by sending a query to the database server 104. In an embodiment, the query is transmitted using the transceiver 206. The transceiver 206 may further receive the historical medical records of the one or more second patients from the database server 104. In an embodiment, the processor 202 may segregate the historical medical records of the one or more second patients into at least two classes, namely the class A and class B historical medical records as discussed above. For example, class A historical medical records may comprise historical medical records of the one or more second patients who had developed medical complications, while the one or more second patients were in the critical care unit (under medical observations). Class B historical medical records may comprise historical medical records of the one or more second patients who did not develop medical complications, while the one or more second patients were in critical care unit (under medical observations). For example, there are 600 second patients out of whom 350 had developed post-operative complication, such as acute respiratory failure (ARF), when they were under medical observations. In such a scenario, the historical medical records of the 350 second patients are included in class A, while the historical medical records of the 250 second patients are included in class B.

After the segregation of the historical medical records of the one or more second patients, the processor 202 utilizes the class A and class B historical medical records to train the one or more classifiers. In an embodiment, the document processor 212 may extract the one or more headings from the class A (or class B) historical medical records of the one or more second patients. Thereafter, the document processor 212 extracts one or more words (related to medical science) from the phrases documented under each of the extracted one or more headings associated with the class A (or class B) historical medical records. The processor 202 may determine the first feature vector for each of the one or more words. Further, the processor 202 may determine the second feature vector for each of the one or more second patients based on the measure of the one or more physiological parameters for each of the one or more second patients. As the processor 202 has the knowledge of the second patients who had developed complications (class A patients) and the second patients who did not develop the complications (class B patients), the processor 202 may utilize the knowledge and first feature vector and the second feature vector to train the one or more classifiers.

At step 304, the one or more headings are extracted from the one or more medical records of the first patient. In an embodiment, the processor 202 may utilize the document processor 212 to extract the one or more headings from the one or more medical records of the first patient. In an embodiment, the document processor 212 may extract the one or more headings from the one or more medical records using the one or more pre-defined rules/instructions stored in the memory 204. For example, if a word in the beginning of a sentence is followed by a colon, it may be considered as a heading. In an embodiment, the document processor 212 may identify symbols such as ":", paragraph spacing, the sentence before a paragraph begins, etc., to identify the one or more headings. In an embodiment, the document processor 212 may refer to a template of the one or more documents to identify the one or more headings. For example, the template may include predefined headings. In an embodiment, the one or more headings may correspond to one or more medical specialties supported by a medical center where the first patient is under medical observation. The one or more medical specialties may include, but are not limited to, neurology, cardiology, orthopedic, gynecology, gerontology, general medicine, pathology, oncology, urology, etc. The extraction of the one or more headings will be explained with an example in conjunction with FIGS. 4A and 4B.

In certain scenarios, the document may not clearly indicate the headings. Further, the one or more healthcare professionals (e.g., doctors, nurses, medical attenders) may have different ways of documenting the observations. In such a scenario, the document processor 212 may refer to a dictionary to identify one or more synonymous terms in the one or more documents. For example, "CARDIO", "CV", "CARD" all refer to the same heading. Further, the document processor 212 may identify the text written under such words or terms. Thereafter, the document processor 212 may assign the same heading tag to each of the so identified words. In an embodiment, the heading tag may be indicative of the heading under which the one or more words or phrases have been written.

At step 306, the one or more words are extracted from the one or more phrases written under each of the extracted one or more headings. In an embodiment, the processor 202 may utilize the document processor 212 to extract the one or more words from the one or more phrases written under each of the extracted one or more headings. The one or more phrases may correspond to the documentation of observations of the first patient by the one or more healthcare professionals. The processor 202 may utilize the document processor 212 to extract the one or more words from the one or more phrases written under each of the one or more headings associated with the one or more medical records of the first patient. The document processor 212 may utilize the pre-defined rules to extract the one or more words. For example, identifying the one or more words related to the medical field (medically relevant term), removing a stop word from the one or more phrases, or removing a punctuation from the one or more phrases written under each of the one or more headings. The extraction of the one or more words will be explained with an example in conjunction with FIGS. 4A and 4B.

At step 308, a first score is determined for each of the extracted one or more words. In an embodiment, the ALU 208 may determine the first score for each of the extracted one or more words under each of the extracted one or more headings from the one or more medical records of the first patient. In an embodiment, the ALU 208 may determine the first score for each word under each heading based on a count of the each word under the each heading present in the class A and class B historical medical records of the one or more second patients. The ALU 208 may determine the first score for each of the extracted word using the below equation:

$$I_w(H) = n_w(A,H) - n_w(B,H) \quad (1)$$

where, $I_w(H)$: First score of a word, w under a heading, H in a medical record associated with the first patient who is under medical observation;

$n_w(A, H)$: Count of the word, w under the heading, H in the class A (historical medical records of the one or more second patients who had developed medical complications, when the one or more second patients were under medical observation); and $n_w(B, H)$; Count of the word, w under the heading, H in the class B (historical medical records of the one or more second patients who did not develop medical complications, when the one or more second patients were under medical observation).

In an embodiment, the processor 202 may utilize the counter 222 to determine the count of each word. In an embodiment, the counter 222 may count the number of times the word w has appeared under the heading H in the class A (or class B) historical medical records of the one or more second patients. In an embodiment, the ALU 208 may utilize the count of each word determined by the counter 222 to determine the first score of each word under each of the one or more headings of the one or more medical records associated with the first patient.

At step 310, the one or more words under each of the extracted one or more headings are ranked based on the first score. In an embodiment, the processor 202 may utilize the comparator 224 to rank the one or more words under each of the one or more headings. In an embodiment, the comparator 224 may compare the first score of the each word under each heading with the first score of the other words under the same heading. Based on the comparison, the processor 202 may rank the one or more words under each of the one or more headings.

At step 312, a pre-defined number of words are selected from the ranked one or more words under each of the one or more headings. In an embodiment, the processor 202 may select the pre-defined number of words. The remaining of the one or more words under each of the one or more headings may be discarded. In an embodiment, the user may utilize the user-computing device 102 to input a pre-defined criteria for selecting the pre-defined number of words from the ranked one or more words. For example, if there are 50 words under a heading, such as cardio, then the user may provide the input to select only the top ten words. In such a case, the processor 202 selects the top ten words and discards the remaining words under that heading. In an embodiment, the processor 202 may select the pre-defined number of words based on a pre-stored instructions stored in the memory 204.

At step 314, the first feature vector is determined based on the count of the selected one or more words in the one or more medical records (text observation) of the first patient. In an embodiment, the processor 202 may utilize the ALU 208 and the counter 222 to determine the first feature vector associated with the first patient. The first feature vector comprises one or more parameters representing the count of each of the selected one or more words in the one or more medical records (text observation) of the first patient. In an embodiment, it may be possible for the same word to occur more than once under different headings. The counter 222 counts the occurrences of each of the selected one or more words under all headings of the one or more medical records (text observation) of the first patient. Therefore, the first feature vector is determined for each of the one or more selected words in the one or more medical records irrespective of the heading under which the word has been written in the one or more medical records. The processor 202 utilizes the count of each word in the one or more medical records as a parameter of the first feature vector. The determination of the first feature vector will be explained with an illustrative example in conjunction with FIGS. 4A and 4B.

At step 316, the second feature vector is determined based on the statistical parameters associated with the one or more physiological parameters of the first patient. In an embodiment, the ALU 208 may determine the second feature vector based on the statistical parameters associated with the one or more physiological parameters of the first patient. The one or more physiological parameters are measured to help assess the general physical health of the first patient, give clues to possible diseases, and show progress towards recovery. The one or more physiological parameters comprise at least blood pressure, heart rate, respiratory rate, body temperature, and oxygen saturation. The one or more physiological parameters of the first patient is continuously monitored through invasive or non-invasive methods. The processor 202 may utilize the sensor 216 to measure the one or more physiological parameters of the first patient. In an embodiment, the user may provide the measured physiological parameters of the first patient. In another embodiment, the processor 202 may send a query to the user-computing device 102 or the database server 104 to extract the physiological parameters of the first patient. In an embodiment, the statistical parameters may be determined by performing one or more mathematical operations on the one or more physiological parameters of the first patient. In an embodiment, the processor 202 may obtain the measured/observed/recorded data corresponding to the physiological parameters over a period of time associated with the first patient. Thereafter, the processor 202 may perform one or more mathematical operations such as mean, standard deviation, median, etc., on the obtained data (corresponding to physiological parameters) to determine the statistical parameters. In an embodiment, the one or more mathematical operations may comprise, but not limited to, determining a maximum or minimum value or a difference between maximum and minimum values, fitting a Gaussian distribution to data, determining a linear regression on the data, etc. In another embodiment, the processor 202 may utilize an algebraic graph theory to determine the statistical parameters of the one or more physiological parameters. The algebraic graph theory involves the use of at least one of linear algebra, group theory, and graph invariant to determine the one or more statistical parameters. In an embodiment, the user may provide an input to select from the various operations that may be needed to be performed on the one or more physiological parameters to extract the statistical parameters. In an embodiment, the processor 202 may utilize the pre-stored instructions to determine the statistical parameters of the one or more physiological parameters. The determined statistical parameters are used to obtain the second feature vector.

At step 318, the health condition of the first patient is predicted. In an embodiment, the processor 202 may utilize the one or more trained classifiers to predict the health condition of the first patient. The one or more classifiers may be implemented using one or more machine learning algorithms. For example, support vector machine (SVM), logistic regression (LR), random forest (RF), etc. In an embodiment, the classifiers may be modeled based on Bayes theorem. As discussed above, the one or more classifiers are trained using different classes of the historical medical records (class A and class B historical medical records). In an embodiment, the processor 202 may utilize natural language processing and supervised machine learning algorithms to train the one or more classifiers. Thereafter, the processor 202 utilizes the one or more trained classifiers to predict the health condition of the first patient based on the analysis of at least one of, but not limited to, the first feature vector, the second feature vector, the historical medical records of the one or more second patients, and the one or more medical records of the first patient. In an embodiment, the processor 202 may also predict morbidity, a length of hospital stay, and a risk of acquiring complications by the first patient who is under medical observation.

A person skilled in the art would understand that the scope of the disclosure should not be limited to the prediction of the health condition of the first patient who is under medical observation in the ICU. In an embodiment, the disclosed method and system may be utilized to predict the health condition of the first patient who is undergoing treatment (not necessarily in the ICU) in the hospitals. In another embodiment, the disclosed method and system may be utilized to predict the health condition of the first patient who is undergoing the treatment at a second place such as, but not limited to, a medical camp, his/her house, or like.

Figure 4A:
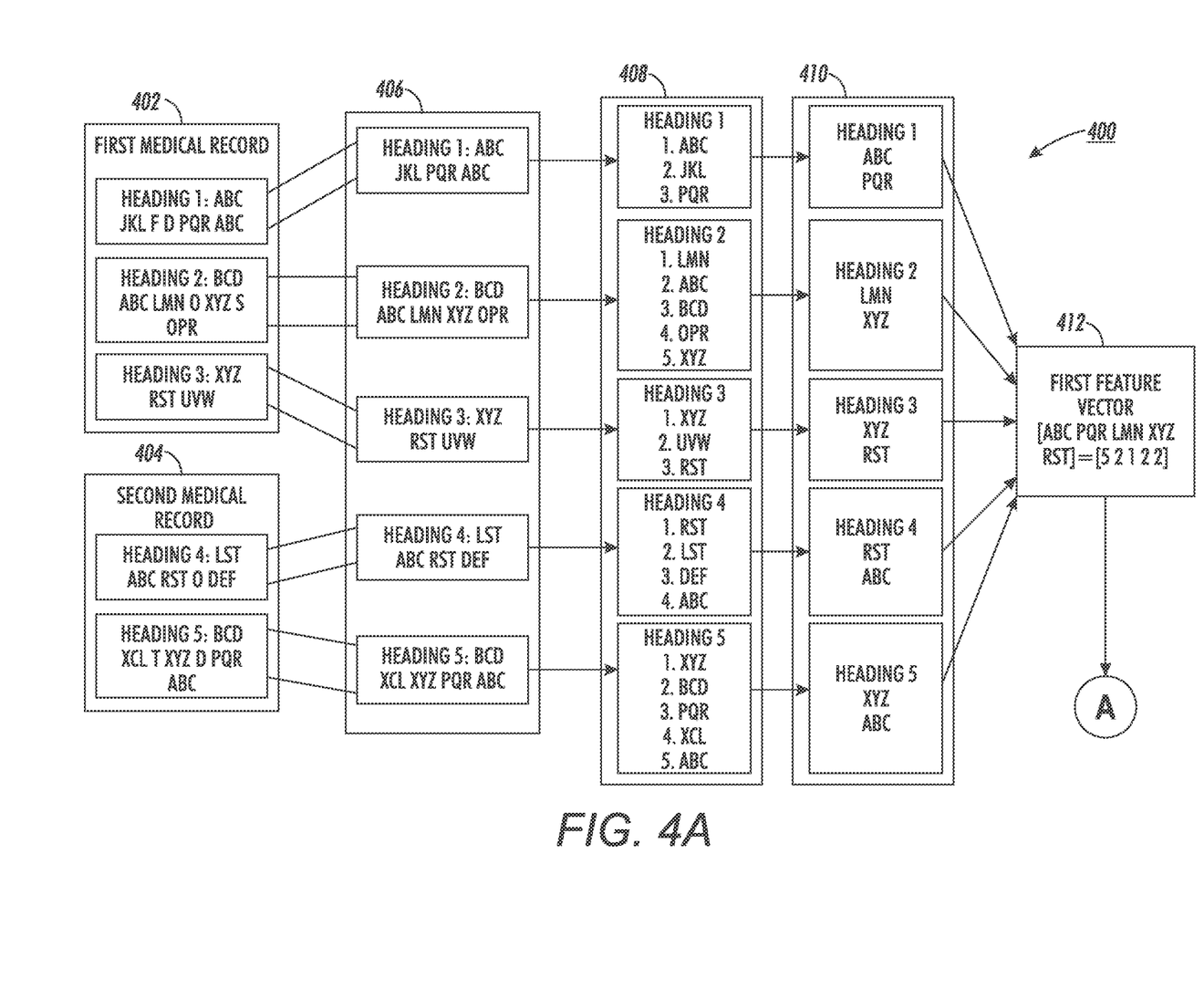
FIGS. 4A and 4B are block diagrams illustrating an example scenario for predicting a health condition of a first patient, in accordance with at least one embodiment.
Figure 4B:
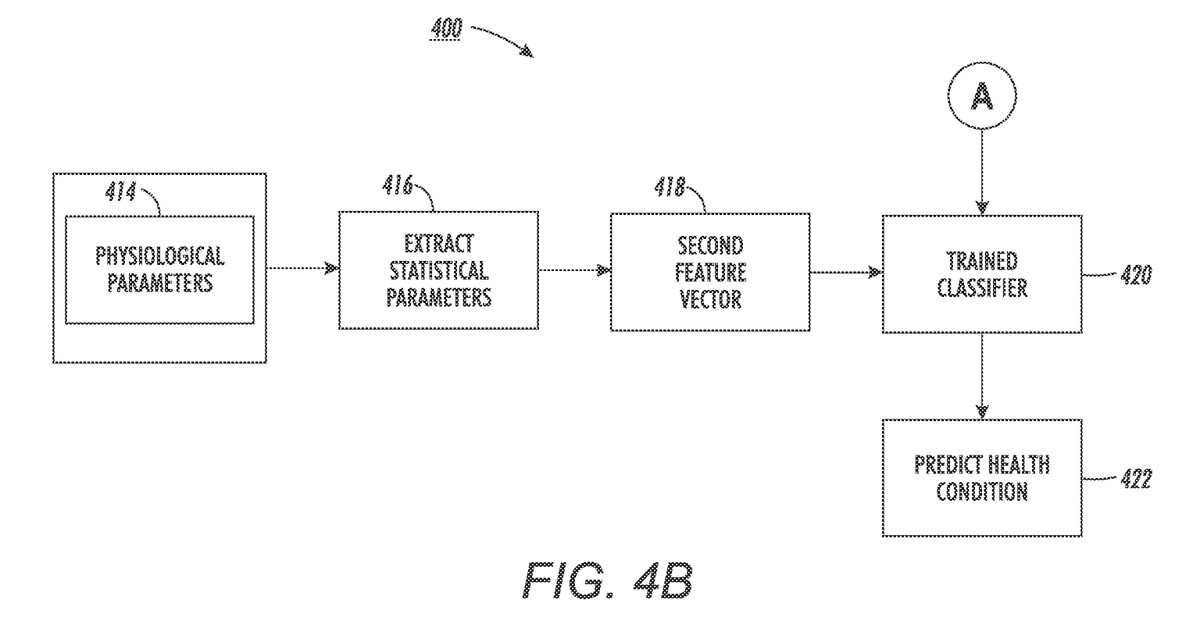

FIGS. 4A and 4B are block diagrams illustrating an example scenario for predicting the health condition of the first patient, in accordance with at least one embodiment. The block diagram 400 is described in conjunction with FIG. 1, FIG. 2 and FIG. 3.

The one or more medical records of the first patient comprise at least two medical records such as a first medical record 402 and a second medical record 404. The first medical record 402 comprises three headings such as heading 1, heading 2, and heading 3. The second medical record 404 comprises two headings such as heading 4 and heading 5. Each heading comprises one or more phrases written under it, as shown in first and second medical records (denoted by 402 and 404, respectively). The processor 202 utilizes the document processor 212 to extract the one or more words under each heading from each of the medical records (depicted by 406). For example, heading 1 comprises the extracted one or more words such as ABC, JKL, PQR, and ABC.

Post extraction of the one or more words, the processor 202 utilizes the ALU 208 and the counter 222 to determine the first score of each word under each heading. The first score of each word is determined as discussed above in step 308. Thereafter, the processor 202 ranks the one or more words based on the first score of each word under each heading (depicted by 408). For example, ABC is ranked first (ABC is having highest first score), JKL is ranked second, and PQR is ranked third (PQR is having lowest first score) under heading 1 (depicted in 408). Similarly, the processor 202 ranks the one or more words under each heading as shown in 408.

Post ranking of the words under each heading, the processor 202 selects a pre-defined number of words from the ranked one or more words under each heading. In the ongoing example, the processor 202 selects a word from the top and a word from the bottom of the ranked words. For example, the words ABC and PQR are selected from the ranked words under heading 1 (depicted in 410). Similarly, the processor 202 selects the one or more words under each heading as shown in 410. Thereafter, the processor 202 determines a first feature vector 412. The processor 202 utilizes the ALU 208 and the counter 222 to determine the first feature vector 412. The first feature vector 412 is determined as discussed above in step 314. The first feature vector 412 comprises the selected one or more words. The first feature vector comprises the one or more parameters (feature value) representing the count each of the selected one or more words in the one or more medical records of the first patient. For example, the word ABC has occurred five times in the two medical records (first medical record and second medical record) of the first patient. Therefore, the feature value corresponding to the word ABC is five. Similarly, the ALU 208 determines the feature value of each of the selected words and thereafter determines the first feature vector 412 as a set of individual feature values of the selected one or more words.

In an embodiment, the processor 202 may utilize one or more sensors such as the sensor 216 to measure the one or more physiological parameters of the first patient. The processor 202 extracts the statistical parameters (depicted by 416) from the one or more physiological parameters (depicted by 414) such as blood pressure, heart rate, respiratory rate, body temperature, and oxygen saturation. Thereafter, the processor 202 determines a second feature vector 418 based on the extracted statistical parameters. Thereafter, the processor 202 utilizes the one or more trained classifiers, such as a trained classifier 420, to analyze at least one of the first feature vector (depicted by 412), the second feature vector (depicted by 418), the historical medical records of the one or more second patients, and the one or more medical records of the first patient (e.g., the first medical record 402 and the second medical record 404). Based on the analysis, the processor 202 predicts the health condition of the first patient who is under medical observation (depicted by 422).

Various embodiments of the disclosure lead to the prediction of the health condition of a patient who is under medical observation. The disclosed method utilizes the one or more medical records of the patient such as the text sources of information (nursing notes, investigative reports, etc.) to predict the postoperative health condition of the patient. The disclosed method further utilizes the statistical features extracted from the one or more vital signs (blood pressure, heart rate, respiratory rate, etc.) to predict the health condition of the patient. The disclosed system is a real time clinical surveillance system that attempts to identify emerging complications (e.g., stroke, urinary tract infections, myocardial infarctions, etc.) for the patient under medical observation, so that a risk of complication/medical emergency can be identified and treated before the patient is discharged from the hospital. Further, the disclosed system may help in reducing penalties associated with re-admission of the patient, thereby economizing operations of a medical care center.

The disclosed methods and systems, as illustrated in the ongoing description or any of its components, may be embodied in the form of a computer system. Typical examples of a computer system include a general-purpose computer, a programmed microprocessor, a micro-controller, a peripheral integrated circuit element, and other devices, or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

In order to process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The systems and methods described can also be implemented using only software programming or using only hardware or by a varying combination of the two techniques. The disclosure is independent of the programming language and the operating system used in the computers. The instructions for the disclosure can be written in all programming languages including, but not limited to, "C," "C++," "Visual C++," Java, and "Visual Basic." Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating systems and platforms including, but not limited to, "Unix," "DOS," "Android," "Symbian," and "Linux."

The programmable instructions can be stored and transmitted on a computer-readable medium. The disclosure can also be embodied in a computer program product comprising a computer-readable medium, or with any product capable of implementing the above methods and systems, or the numerous possible variations thereof.

Various embodiments of the methods and systems for predicting a health condition of a patient have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different systems or applications.

Those skilled in the art will appreciate that any of the aforementioned steps and/or system modules may be suitably replaced, reordered, or removed, and additional steps and/or system modules may be inserted, depending on the needs of a particular application. In addition, the systems of the aforementioned embodiments may be implemented using a wide variety of suitable processes and system modules and is not limited to any particular computer hardware, software, middleware, firmware, microcode, or the like.

The claims can encompass embodiments for hardware, software, or a combination thereof.

It will be appreciated that variants of the above disclosed, and other features and functions or alternatives thereof, may be combined into many other different systems or applications. Presently unforeseen or unanticipated alternatives, modifications, variations, or improvements therein may be subsequently made by those skilled in the art, which are also intended to be encompassed by the following claims.

What is claimed is:

1. A method for utilizing sensor data to predict a health condition of a first patient via a combination of bio-sensors and supervised machine learning algorithms, said method comprising:
   extracting, from a database server communicatively coupled to one or more processors, metadata pertaining to historical medical records of one or more second patients, the historical medical records including physiological parameters of the one or more second patients;
   segregating the metadata into a first class and a second class, the first class representing a first portion of the one or more second patients that did not develop a medical condition during their hospital stay, the second class representing a second portion of the one or more second patients that developed a medical condition during their hospital stay;

extracting one or more selected words in the segregated metadata for each of the first class and the second class and determining a first feature vector, for the one or more second patients, based on a count of the selected one or more words in the segregated metadata;

determining a second feature vector, for the one or more second patients, based on the physiological parameters of the one or more second patients;

training one or more supervised machine learning algorithms using the first feature vector and the second feature vector;

obtaining, from one or more bio-sensors coupled to the processor, sensor data corresponding to one or more physiological parameters associated with said first patient;

analyzing, in real-time, the one or more physiological parameters of the first patient using the one or more supervised learning machines trained with the first feature vector and the second feature vector to identify an emerging complication for said first patient;

outputting the identified emerging complication in real-time; and treating the identified emerging complication based on the analysis.

2. The method of claim 1, further comprising:

extracting one or more headings from one or more medical records of said first patient based on one or more predefined rules, wherein each of said one or more headings corresponds to one or more medical specialties supported by a medical center where said first patient is observed; and extracting one or more words from one or more phrases written under each of said extracted one or more headings, wherein said one or more phrases corresponds to documentation of said observation of said first patient by a medical attender, wherein said one or more medical records comprises at least one of a nursing note and an investigative report.

3. The method of claim 2, further comprising scanning, by an image capturing device, said one or more medical records associated with said first patient.

4. The method of claim 2, further comprising determining, by an arithmetic logic unit, a first score for each of said one or more words under each of said extracted one or more headings based on a count of one or more words under said one or more headings in said historical medical records.

5. The method of claim 4, further comprising ranking, by said one or more processors, said one or more words under each of said extracted one or more headings based on said first score.

6. The method of claim 5, further comprising selecting, by said one or more processors, a pre-defined number of said one or more words from said ranked one or more words under each of said extracted one or more headings.

7. The method of claim 6, further comprising determining, by said arithmetic logic unit, a third feature vector associated with said one or more medical records of the first patient based on said count of said selected one or more words in said one or more medical records of said first patient.

8. The method of claim 7, further comprising determining, by said arithmetic logic unit, a fourth feature vector associated with said one or more physiological parameters of the first patient based on statistical parameters associated with each of said one or more physiological parameters of the first patient.

9. The method of claim 8, wherein said one or more processors utilizes one or more supervised machine learning algorithms to predict said health condition of said first patient based on at least one of said third feature vector, said fourth feature vector, said historical medical records, and said one or more medical records of said first patient.

* * * * *